(12) United States Patent
Hirahara (10) Patent No.: US 6,470,623 B1
(45) Date of Patent: Oct. 29, 2002

(54) END SEAL FOR A MANUFACTURED SEED AND A METHOD OF MANUFACTURING AND ATTACHING THE SAME

(75) Inventor: Edwin Hirahara, Chehalis, WA (US)

(73) Assignee: Weyerhauser Company, Federal Way, WA (US)

( * ) Notice: Subject to any disclaimer, the term of this patent is extended or adjusted under 35 U.S.C. 154(b) by 0 days.

(21) Appl. No.: 09/644,252

(22) Filed: Aug. 22, 2000

Related U.S. Application Data (60) Provisional application No. 60/150,284, filed on Aug. 23, 1999.

(51) Int. Cl.[7] ................................................ A01C 1/06
(52) U.S. Cl. ..................................... 47/57.6; 47/DIG. 9
(58) Field of Search ................................ 47/57.6, 58.1; A01C 1/06

(56) References Cited

U.S. PATENT DOCUMENTS

| | | | | |
|---|---|---|---|---|
| 3,690,034 A | * | 9/1972 | Knapp ........................ | 47/57.6 |
| 4,628,633 A | * | 12/1986 | Nilsson ...................... | 57/57.6 |
| 5,250,082 A | * | 10/1993 | Teng et al. .................. | 47/57.6 |
| 5,284,765 A | * | 2/1994 | Bryan et al. ............. | 435/240.4 |
| 5,427,593 A | * | 6/1995 | Carlson et al. .............. | 47/57.6 |
| 5,701,699 A | | 12/1997 | Carlson et al. | |
| 5,799,439 A | * | 9/1998 | MacGregor ................. | 47/57.6 |
| 6,119,395 A | * | 9/2000 | Hartle et al. ................. | 47/57.6 |

FOREIGN PATENT DOCUMENTS

| | | | |
|---|---|---|---|
| WO | WO 92/07457 | 5/1992 | |
| WO | WO 98/33375 | * 8/1998 | ............ A01C/1/06 |

OTHER PUBLICATIONS

Grob, J.A., et al. "Dimensional Model of Zygotic Douglas--Fir Embryo Development," *International Journal of Plant Sciences* 160(4):653–662, 1999.

Timmis R., "Bioprocessing for Tree Production in the Forest Industry: Conifer Somatic Embryogenesis," *Biotechnology Progress* 14(1):156–166, Feb. 1998.

* cited by examiner

*Primary Examiner*—Peter M. Poon
*Assistant Examiner*—Andrea M. Valenti
(74) *Attorney, Agent, or Firm*—Christensen O'Connor Johnston Kindness PLLC (57) ABSTRACT

A method of attaching an end seal (20) to a manufactured seed (22). The method including the steps of positioning a first manufactured seed on a surface (42). The first manufactured seed including a seed coat (24) having an opening (12) and an embryo (30) disposed within the opening. The opening having a location relative to the surface. The method further including prestressing an area (38) of a sheet (50) and positioning the sheet on the first manufactured seed to substantially center the area over the opening, such that the embryo is located below the area. The method also including the step of attaching the sheet to the first manufactured seed to seal the opening.

29 Claims, 6 Drawing Sheets

END SEAL FOR A MANUFACTURED SEED AND A METHOD OF MANUFACTURING AND ATTACHING THE SAME

CROSS-REFERENCE TO RELATED APPLICATION

This application claims the benefit of Provisional Patent Application No. 60/150,284, filed Aug. 23, 1999, which is incorporated herein by reference.

FIELD OF THE INVENTION

The present invention relates generally to manufactured seeds and, more particularly, to an end seal for a manufactured seed.

BACKGROUND OF THE INVENTION

Asexual propagation for plants has been shown for some species to yield large numbers of genetically identical embryos, each having the capacity to develop into a normal plant. Such embryos must usually be further cultured under laboratory conditions until they reach an autotrophic "seedling" state characterized by an ability to produce their own food via photosynthesis, resist desiccation, produce roots able to penetrate soil and fend off soil microorganisms. Some researchers have experimented with the production of the artificial seeds, known as manufactured seeds, in which individual plant somatic or zygotic embryos are encapsulated in a seed coat. Examples of such manufactured seeds are disclosed in U.S. Pat. No. 5,701,699, issued to Carlson et al., the disclosure of which is hereby expressly incorporated by reference.

Typical manufactured seeds include a seed coat, synthetic gameophyte and a plant embryo. The seed coat typically is a cylindrical capsule having a closed end and an open end. The synthetic gameophyte is placed within the seed coat, such that the gameophyte substantially fills the interior of the seed coat. A longitudinally extending hard porous insert, commonly known as a cotyledon restraint, may be centrally located within the synthetic gameophyte and includes a centrally located cavity extending partially through the length of the cotyledon restraint. The cavity is sized to receive the plant embryo therein. The well known plant embryo includes a radicle end and a cotyledon end. The plant embryo is deposited within the cavity of the cotyledon restraint cotyledon end first. The plant embryo is then sealed within the seed coat by at least one end seal. There is a weakened spot in the end seal to allow the radicle end of the embryo to penetrate the end seal.

Typically, the end seal is formed from a sheet of polymer material. In the past, a mechanical rod is used to stretch and, therefore, thin or weaken a small spot in the center of the seal. The weakened spot in the end seal is desirable because as the embryo begins to grow, the weakened spot permits tangential distribution of load to assist in the breakthrough of the embryo through the end seal.

A disk of predetermined diameter is then cut from the polymer sheet with the weakened spot in the center of the disk forming the end seal. After the end seals are cut from the polymer sheet, they are pushed out of a punch cavity with a rod and then fall by gravity on top of the seed coat. The seed coat with the end seal is then transferred to a separate station to heat fuse the end seals to the seed coats. Although such a process is effective at forming and sealing end seals to the seed coat of a manufactured seed, it is not without its problems.

First, it is difficult to maintain the exact location of the opening into the cavities of the cotyledon restraint as the manufactured seed passes through the production line. Second, the placement of the end seal over the seed coat is not reliable. Additionally, the end seals tend to stick to the punch or punch cavity. Further, fusing of the end seals to the seed coats is difficult and time consuming because the end seals must be heated to a point where the end seal is fused to the seed coat without damaging the dome or weakened area itself. Sometimes the fusing process melts holes in the weakened spot. Finally, the fusing process may cause damage to the plant embryo itself. As a result, mass production of manufactured seeds is not only time consuming, but also expensive.

Thus, there exists a need for a method of manufacturing and attaching an end seal to a seed coat of a manufactured seed that can produce and attach a large number of end seals to a manufactured seed at a relatively low cost, a high degree of reliability and without damaging the plant embryo located within the seed coat.

SUMMARY OF THE INVENTION

In accordance with the present invention, a method of manufacturing and attaching an end seal to a manufactured seed coat is provided. The method includes the step of positioning a first manufactured seed coat having an opening and a perimeter. The method also includes the step of prestressing an area of a sheet of material. The sheet is positioned on the first manufactured seed to substantially center the area over the manufactured seed coat opening. Finally, the method includes the step of attaching the polymeric sheet to the first manufactured seed coat to seal the manufactured seed coat opening.

In one embodiment, the step of prestressing the area of the sheet includes ablating a predetermined area of the sheet. The predetermined area of the sheet is located according to the location of the opening of the seed coat.

In yet another embodiment of the present invention, the method further includes the step of placing the sheet between first and second templates before ablating the predetermined area of the sheet, the first and second templates each having a bore extending therethrough. The step of ablating the predetermined area of the sheet forms an annular collar on at least one surface of the sheet.

In still yet another embodiment of the present invention, the step of attaching the sheet to the manufactured seed includes fusing the sheet to the manufactured seed to seal the embryo within the manufactured seed.

The present invention is also directed to the resulting manufactured seed that includes a seed coat having a length and a cavity extending from one end of the seed coat partially through the length of the seed coat. The manufactured seed also includes an embryo disposed within the cavity and an end seal attached to one end of the seed coat. The end seal includes an ablated area, wherein the ablated area is located on a predetermined portion of the end seal to position the ablated area substantially over the opening of the cavity.

The method of attaching an end seal to a manufactured seed coat, as well as the resulting manufactured seed, form in accordance with the present invention has several advantages over currently available methods. The present invention is more accurate because it prestresses a predetermined area of the polymeric sheet according to predetermined coordinates of the opening in the manufactured seed coat. Also, the problem of misaligning the end seals with the seed coats is minimized because the prestressed area is located according to known coordinates and held in place by a template. Further, no moving parts are used to create the weakened spot, fuse the end seal to the seed coat and cut away any excess material from the end seal, thereby ensuring increased reliability.

Thus, a method of attaching end seals to a manufactured seed, and the resulting manufactured seed, in accordance with the present invention has a high degree of reliability, is able to precisely locate and mass produce end seals and reliably attach the end seals to a seed coat, and minimizes the risk of damaging or contaminating the plant embryo during the process of manufacturing the seed.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
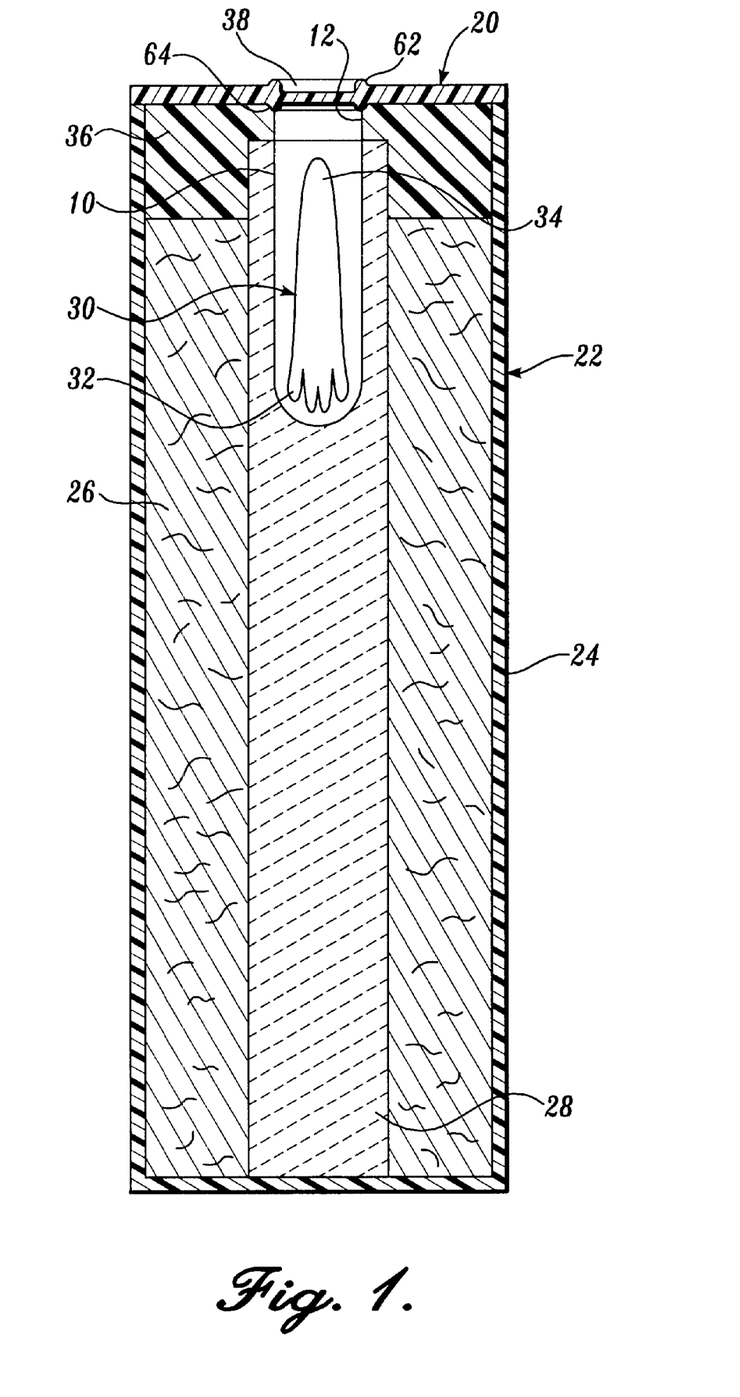
FIG. 1 is a cross-sectional side view of a manufactured seed with an end seal formed in accordance with the present invention.

FIG. 1 illustrates an end seal 20 constructed in accordance with the present invention for a manufactured seed 22. As is disclosed in U.S. Pat. No. 5,701,699, issued to Carlson et al., the disclosure which is hereby incorporated by reference, well known manufactured seeds 22 include a seed coat 24, synthetic gameophyte 26, a cotyledon restraint 28, a plant embryo 30, and a primary seal 36.

The cotyledon restraint 28 is suitably manufactured from a hard porous material and includes a longitudinally extending cavity 10. The cavity 10 extends through the primary seal 36 and partially through one end of the cotyledon restraint 28. The open end of the cavity 10 is known as a cotyledon restraint opening 12. The cavity 10 is sized to receive the plant embryo 30 therein. The plant embryo 30 includes a cotyledon end 32 and a root end 34.

The cotyledon restraint opening 12 is sealed by the end seal 20. The end seal 20 is suitably formed from a sheet, of polymeric film and includes a prestressed area 38. The prestressed area 38 is centrally located above the cotyledon restraint opening 12, as is disclosed in greater detail below.

Manufacture and attachment of the end seal 20 may be best understood by referring to FIGS. 2–5. Manufacture and attachment of the end seal 20 includes a template assembly 40 sized to be received on a receptacle tray 42. The receptacle tray 42 has a plurality of vertically extending bores 44 extending partially through the thickness of the receptacle tray 42. Each bore 44 is sized to receive an unsealed manufactured seed 22 therein. The unsealed manufactured seeds 22 may either be manually placed within the receptacle tray 42 or may be mechanically inserted therein.

Figure 2:
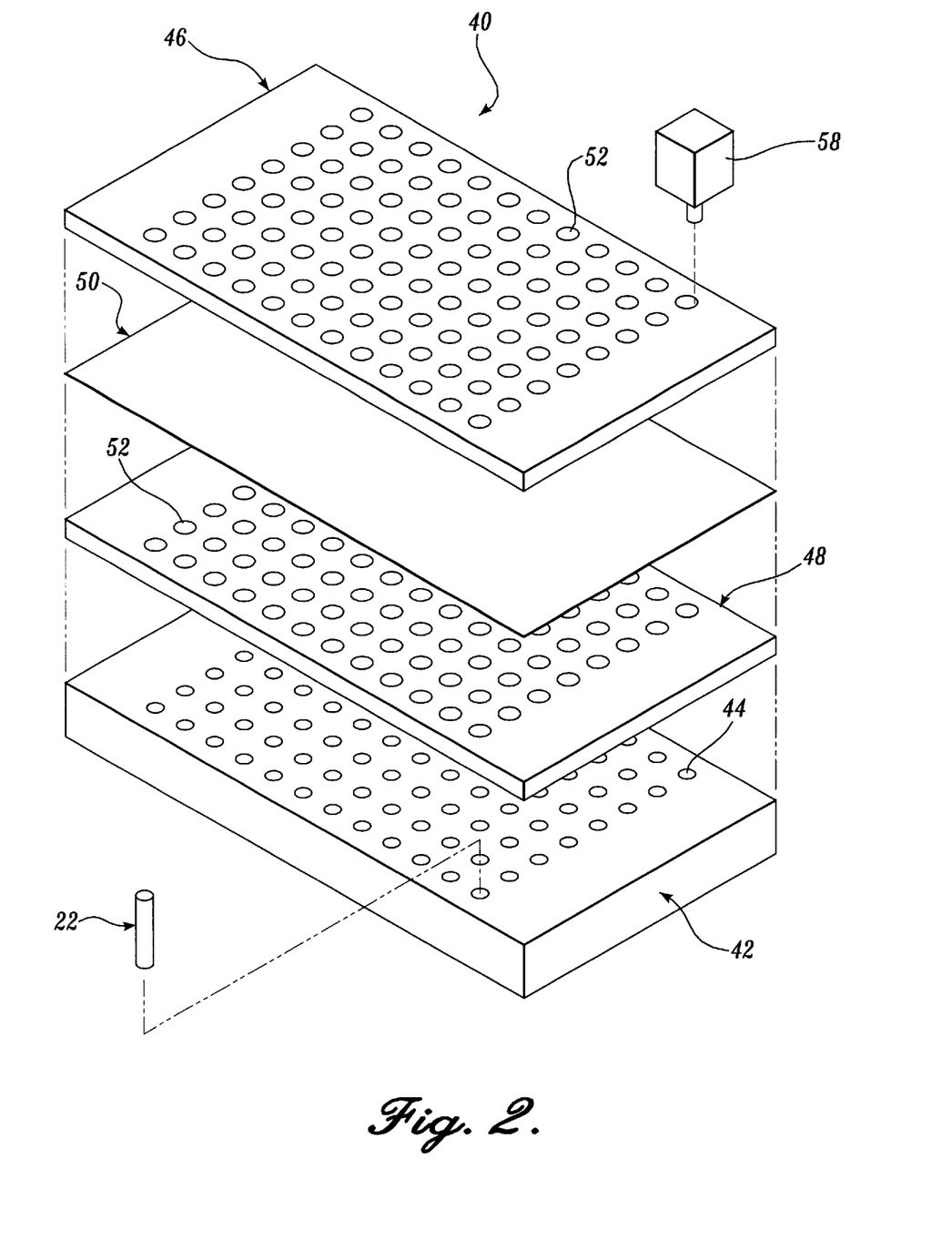
FIG. 2 is an exploded view of an end seal manufacture and attachment assembly formed in accordance with the present invention.

The rectangular template assembly 40 also includes first and second templates 46 and 48 and a sheet 50 of polymer film. The first and second templates 46 and 48 are identically configured and include a plurality of bores 52 extending vertically through each template 46 and 48. The size or topology of the first and second templates 46 and 48 may be different. The bores 52 of the first and second templates 46 and 48 coaxially align in the vertical direction with the bores 44 of the receptacle tray 42 when the template assembly 40 is attached to the receptacle tray 42.

Figure 3:
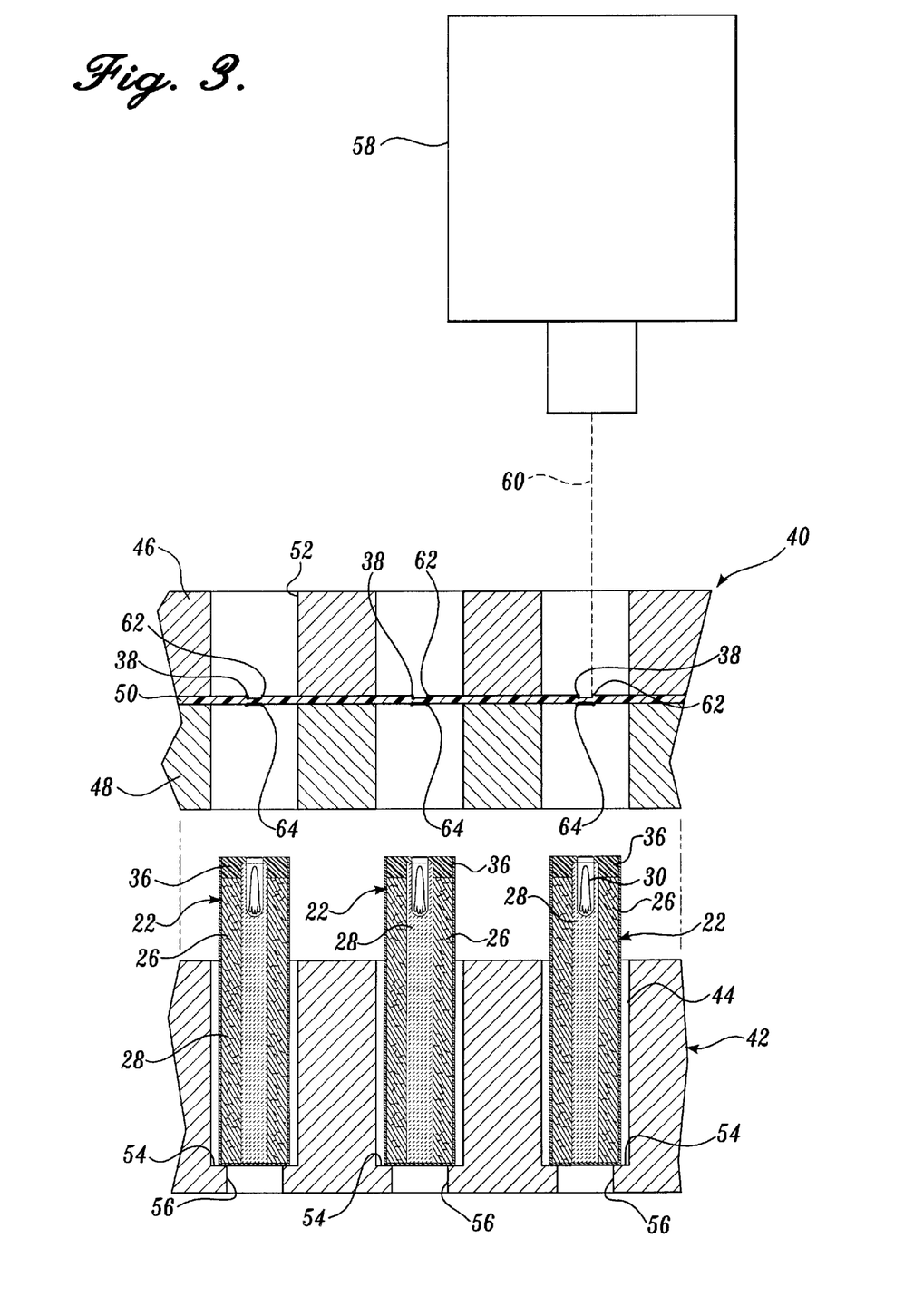
FIG. 3 is a cross-sectional partial side view of an end seal manufacture and attachment assembly formed in accordance with the present invention.

As may be best seen by referring to FIG. 3, the sheet 50 of polymer material is sandwiched between the upper surface of the second template 48 and the lower surface of the first template 46. As sandwiched between the first and second templates 46 and 48, a portion of the sheet 50 is exposed through the bores 52 of the first and second template 46 and 48. As noted above, during the manufacture of the end seal 20, the unsealed manufactured seeds 22 are inserted in the bores 44 of the receptacle tray 42. The manufactured seeds 22 are seated in the bores 44 on an annular shoulder 54. Centrally located in each bore 44 is a passage 56 for assisting in removing the manufactured seeds 22 from the bores 44 after the end seal 20 is applied, as is described in greater detail below.

The template assembly 40 is held in close proximity to the receptacle tray 42 and the prestressed area 38 is suitably formed in the sheet 50 by a well known laser 58. Although the prestressed area is suitably formed by a laser, other methods of prestressing the end seal, such as using a rod to stretch and, hence, thin or weaken a spot, are also included within the scope of the invention. Earlier in the process, the receptacle tray 42 is imaged and the location of each cotyledon restraint opening 12 is determined and stored by a well known position compensation system (not shown), such as a Model F350, F300 or F200 manufactured by Omron Vision Systems. The precise location of each cotyledon restraint opening 12 is relayed back to a well known software program to control the laser 58. As a result, the prestressed area 38 in each end seal 20 is precisely located according to the predetermined location of the openings 12, such that when the end seal 20 is attached to the manufactured seed 22, the prestressed area 38 is centrally located above the opening 12. During this step, the laser 58 applies a laser beam 60 to the sheet 50 causing the area of the sheet 50 subjected to the laser beam 60 to be ablated. As a result, this area of the sheet 50 thins and creates upper and lower annular collars 62 and 64 on the upper and lower surfaces of the sheet 50. The laser beam 60 is applied to this area to prestress this area, such that the root end of the plant embryo 30 will have an easier time to breakthrough at a predetermined force, as is described in greater detail below.

Figure 4:
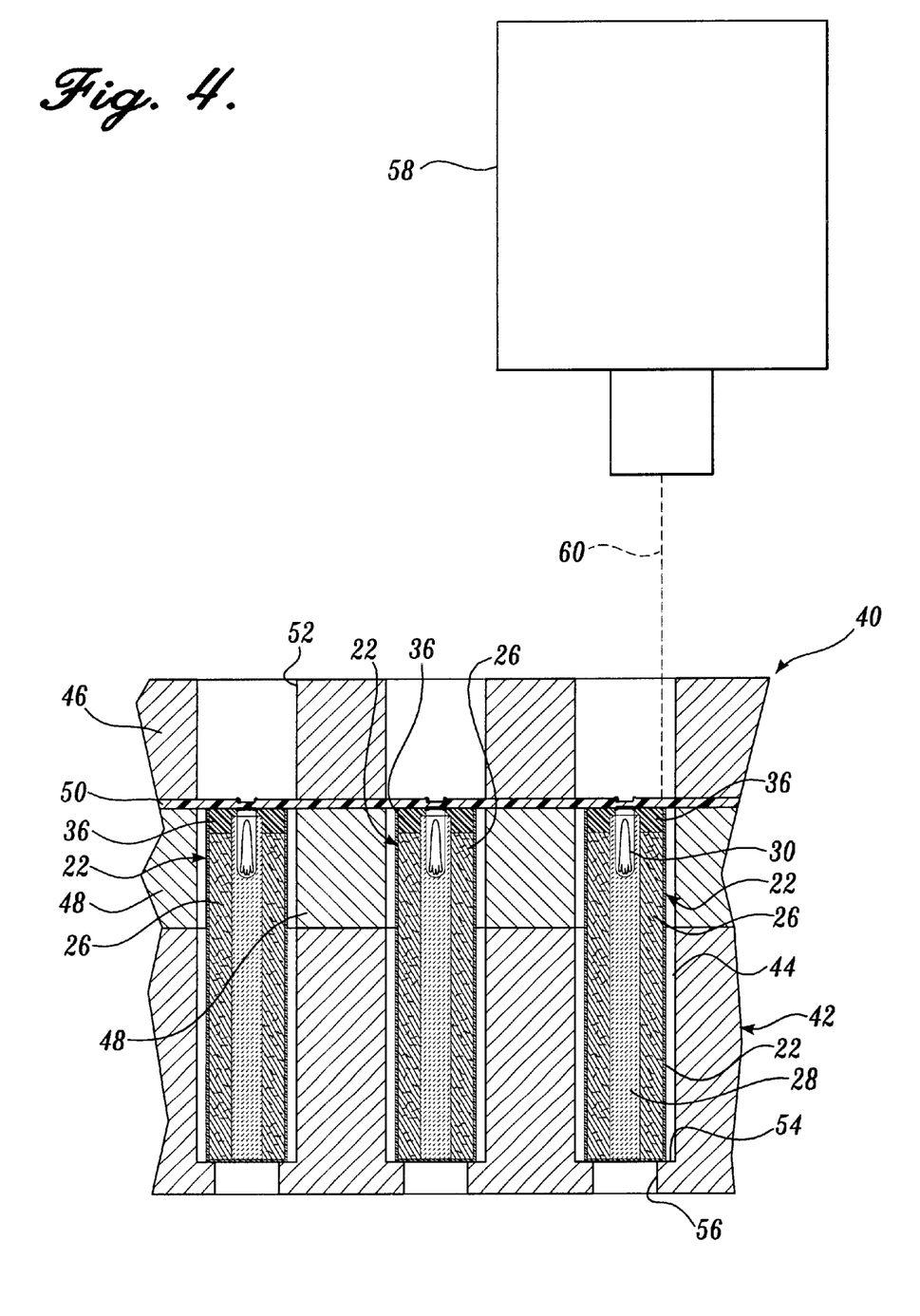
FIG. 4 is a cross-sectional partial side view of an end seal manufacture and attachment assembly formed in accordance with the present invention showing the attachment of the end seal to the seed coat.

As seen best by referring to FIG. 4, after the sheet 50 has been laser treated to define a plurality of prestressed areas 38, the template assembly 40 is placed into contact with the receptacle tray 42. As received on the receptacle tray 42, the manufactured seeds 22 extend upwardly within the bores 52 of the template assembly 40 until the upper end of the manufactured seed 22 is in contact with the lower surface of the sheet 50. In this position, the prestressed areas 38 are centrally located above the plant embryo 30.

The receptacle tray 42 with the manufactured seeds 22 received therein is imaged by a well known sensor (not shown) and the precise location of the cotyledon restraint opening 12 is precisely measured and stored by the position compensation system described above. The stored information is fed to the laser 58, such that the exact diameter and location of the prestressed areas 38 on the sheet 50 is calculated and precisely located. As a result, because the receptacle tray 42 is imaged with the manufactured seeds 22 seeded therein, any variation of the location of the opening to the cotyledon restraint 28 may be compensated by positioning the laser 58 to form the prestressed area 38 in the appropriate location on the sheet 50.

When the template assembly 40 is received on the receptacle tray 42, the lower collar 64 of the prestressed area 38 is received partially within the opening of the cotyledon restraint 28 to ensure a tight seal therebetween. As noted above, each prestressed area 38 is precisely located in the center of the opening in the cotyledon restraint 28 to ensure that the root end 34 of the plant embryo 30 is located directly below each prestressed area 38.

Still referring to FIG. 4, the end seal 20 is sealed to the seed coat 24 by the laser 58. In this attachment step, the laser beam 60 is directed to heat, but not ablate, the polymer film around the area that contacts the primary end seal 36 and around the area outside the prestressed area 38 surrounded by the collar 62. As a result, the laser 58 fuses the polymer sheets to the manufactured seed 22.

After a portion of the sheet 50 has been fused to the manufactured seed 22, the excess polymer material of the sheet 50 outside the perimeter of each manufactured seed 22 is cutaway by the laser 58. After trimming away excess material, the template assembly 40 is separated from the receptacle tray 42 and the excess material is removed. A slight pressure of air may be filtered through the passage 56 to assist in removing the now sealed manufactured seed from within the bores 44 of the receptacle tray 42.

Figure 5:
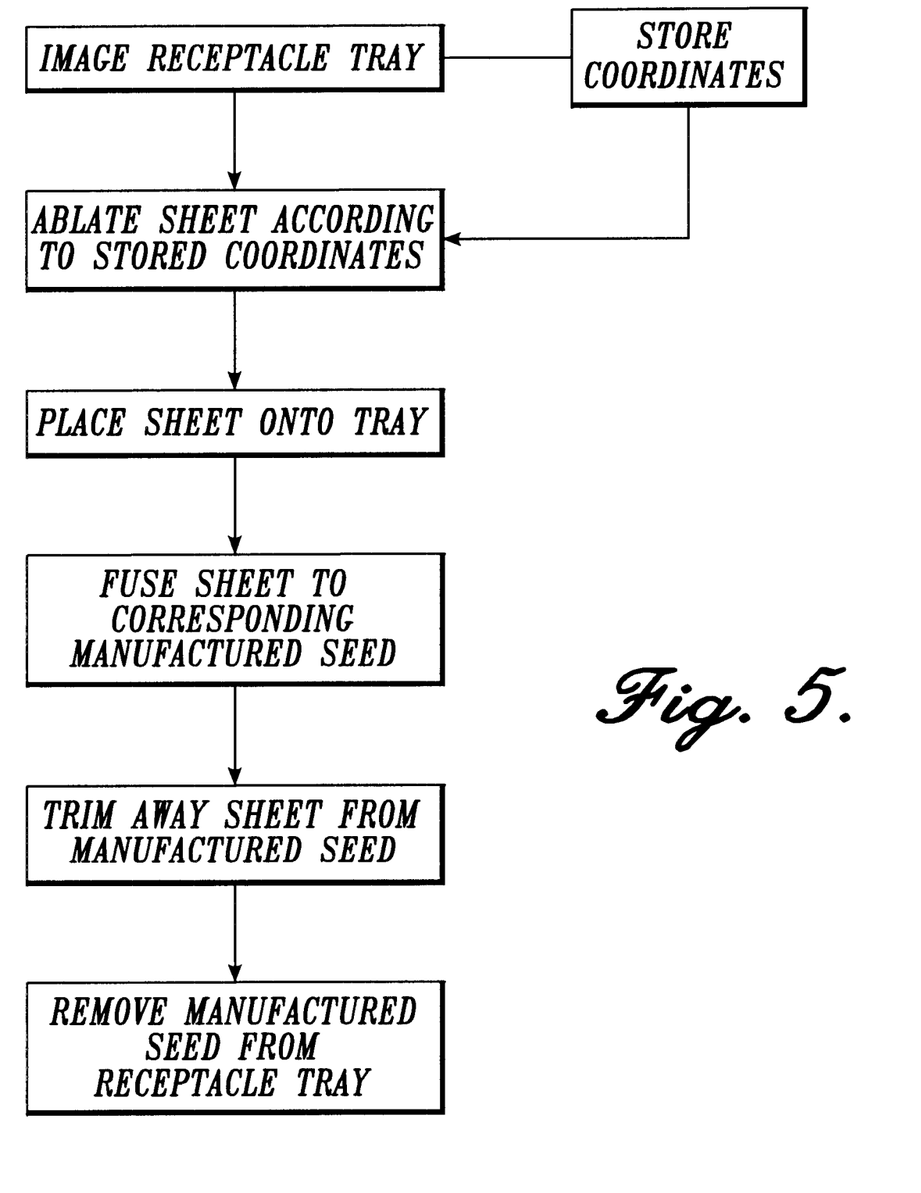
FIG. 5 is a flow diagram of a portion of the method of attaching an end seal to a manufactured coat.

A summary of the method of the present invention may be best understood by referring to FIG. 5. As described in greater detail above, the receptacle tray 42 is imaged by a well-known imager to obtain the coordinates of each bore 44 of the receptacle tray 42. Such coordinates are stored for accurate location of the prestressed area 38. The polymer sheet 50, sandwiched between the first and second templates 46 and 48, is ablated by the laser 58. The location of the prestressed area 38 is precisely located according to the stored coordinates of the bore 44. The polymer sheet 50 is placed onto the receptacle tray 52, such that the polymer sheet 50 is placed into contact with the opened end of the seed 22. The polymer sheet 50 is fused to the seed 22 by the laser beam 60. The laser beam 60 trims around the outside perimeter of the seed 22 to cut away excess portions of the polymer sheet 50. Finally, the manufactured seed 22 is removed from the receptacle tray 42 by a slight pressure of air filtered through the passage 56.

Figure 6:
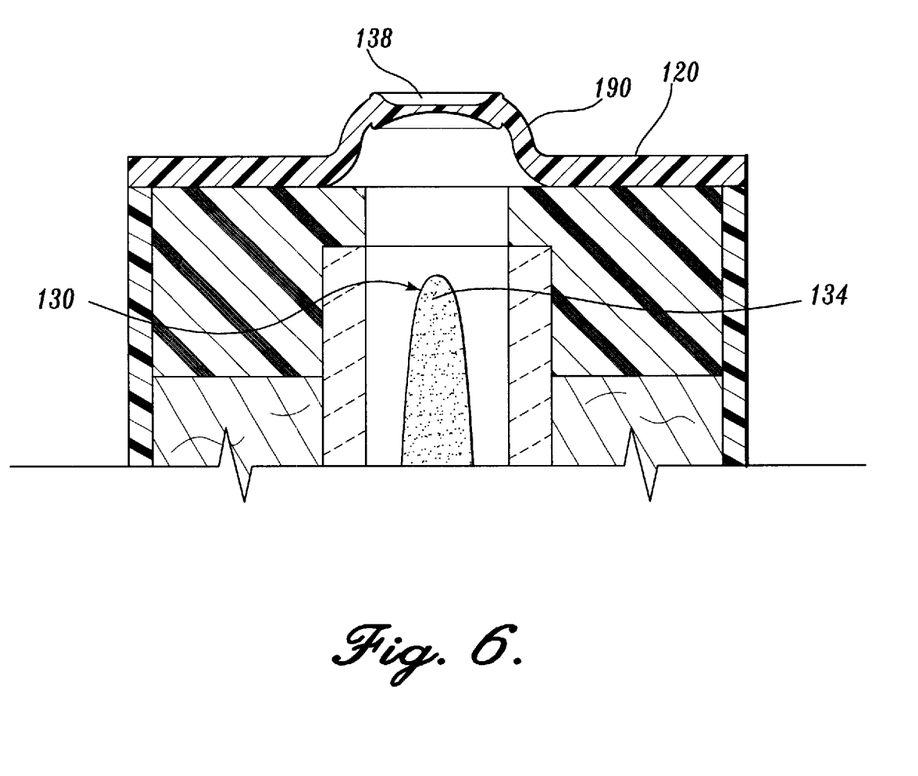
FIG. 6 is a central cross sectional view of an alternate embodiment of an end seal constructed in accordance with the present invention.

Referring to FIG. 6, a second embodiment of an end seal 120 formed in accordance with the present invention will now be described in greater detail. The end seal 120 of the second embodiment is identical in materials and operation as the first embodiment described above with the following exception. The prestressed area 138 is centrally located in a dome area 190 formed in the end seal 120. The domed area 190 is preformed in the sheet before the sheet is ablated by a laser. Suitably, a sheet of polymeric material may be imprinted with a plurality of dimples, wherein the dimples form the domed area 190. Each dimple creates a depression into the sheet 50, without piercing the sheet 50. After the formation of dimples in the sheet 50, the sheet may be sandwiched between templates as taught above and subjected to ablation by a well-known laser. This results in an end seal 120 that includes both a domed area 190 and a prestressed area 138 centrally located in the domed area 190.

During the growth of the embryo 130, the root end 134 expands into the domed area 190, wherein the domed area 190 assists in directing the growth of the root end 134 into the prestressed area 138. This results in a substantially controlled environment, wherein the growth of the plant embryo 130 is substantially directed towards the prestressed area 138.

The previously described version of the present invention provides several advantages over currently available methods of manufacturing and attaching an end seal to a manufactured seed. Such a method has the advantage of making and attaching the end seal in one operation, as well as making the weakened or prestressed area more quickly and more uniformly than currently available systems. Also, because the prestressed area is weakened, as the plant embryo begins to grow, it permits tangential distribution of load to assist in the breakthrough of the plant embryo through the end seal. Additionally, such a system permits large production of end seals for manufactured seeds. Further, no moving parts are use to create the weakened spot, fuse the end seal and the seed coat and cut away any excess material from the end seal, thereby ensuring increased reliability. Thus, the manufacture and attachment of end seals for a manufactured seed formed in accordance with the present invention, is economical to produce, has a high degree of reliability and minimizes the risk of damaging or contaminating the plant embryo during the sealing process of manufacturing the seed.

From the foregoing description, it can be seen that the manufacture and attachment of an end seal to a manufactured seed formed in accordance with the present invention incorporates many novel features and offers significant advantages over currently available systems. While the presently preferred embodiments of the invention have been illustrated and described, it is to be understood that within the scope of the appended claims, various changes can be made therein without departing from the spirit of the invention.

The embodiments of the invention in which an exclusive property or privilege is claimed are defined as follows:

1. A method of attaching an end seal to a manufactured seed, the method comprising the steps of:
   (a) positioning a manufactured seed on a tray, the manufactured seed including a seed coat having an opening and an embryo disposed within the opening, the opening having a location relative to the tray;
   (b) positioning a sheet between first and second templates, each template having a bore extending therethrough to expose a predetermined area of the sheet;
   (c) prestressing the predetermined area of the sheet;
   (d) positioning the sheet on the manufactured seed to substantially center the predetermined area over the opening such that the embryo is located below the predetermined area; and
   (e) attaching the sheet to the manufactured seed to seal the opening.

2. The method of claim 1, wherein the predetermined area of the sheet includes an indentation.

3. The method of claim 2, wherein the step of prestressing the predetermined area of the sheet includes ablating the predetermined area by a laser.

4. The method of claim 1, wherein the predetermined area of the sheet is located according to the location of the opening of the seed coat.

5. The method of claim 4, wherein the step of prestressing the predetermined area of the sheet includes ablating the predetermined area by a laser.

6. The method of claim 5, wherein the step of prestressing the predetermined area of the sheet forms an annular collar on at least one surface of the sheet.

7. The method of claim 6, wherein the step of attaching the sheet to the manufactured seed includes placing the annular collar within the opening of the seed coat.

8. The method of claim 7, further comprising heating areas of contact between the sheet and the manufactured seed by a laser.

9. A method of attaching an end seal to a manufactured seed, the method comprising the steps of:
   (a) positioning a first manufactured seed on a surface, the first manufactured seed including a seed coat having an opening and an embryo disposed within the opening, the opening having a location relative to the surface;
   (b) prestressing an area of a sheet;
   (c) positioning the sheet on the first manufactured seed to substantially center the area over the opening such that the embryo is located below the area;
   (d) attaching the sheet to the first manufactured seed to seal the opening;
   (e) placing the sheet between a first template and the first manufactured seed before prestressing an area of the sheet, the first template having a bore extending therethrough; and
   (f) placing a second template between the sheet and the first manufactured seed such that the sheet is sandwiched between the first and second templates, the second template having a bore extending therethrough.

10. The method of claim 9, wherein the step of prestressing the area of a sheet includes ablating a predetermined area of the sheet.

11. The method of claim 10, wherein the predetermined area of the sheet is located according to the location of the opening of the seed coat.

12. The method of claim 9, wherein the step of prestressing the area of a sheet includes forming a dimple in the area of the sheet.

13. The method of claim 12, further comprising the step of ablating the dimple to centrally locate the prestressed area in the dimple.

14. The method of claim 9, wherein the bores of the first and second templates align to expose a predetermined area of the sheet.

15. The method of claim 14, wherein the predetermined area of the sheet is located according to the location of the opening of the seed coat.

16. The method of claim 15, wherein the step of prestressing the area of a sheet includes ablating the predetermined area of the sheet sandwiched between the first and second templates.

17. The method of claim 15, further comprising the step of forming a dimple in the predetermined area of the sheet before prestressing the predetermined area of the sheet.

18. The method of claim 17, wherein the step of prestressing the area of the sheet includes ablating the predetermined area of the sheet.

19. The method of claim 15, wherein the step of prestressing the area of a sheet includes ablating the predetermined area of the sheet by a laser.

20. The method of claim 16, wherein the step of ablating the predetermined area of the sheet forms an annular collar on at least one surface of the sheet.

21. The method of claim 20, wherein the step of attaching the sheet to the first manufactured seed includes inserting the annular collar within the opening of the seed coat.

22. The method of claim 20, wherein the step of attaching the sheet to the first manufactured seed includes fusing the sheet to the first manufactured seed to seal the embryo within the first manufactured seed.

23. The method of claim 22, further comprising heating areas of contact between the sheet and the first manufactured seed by a laser.

24. A method of attaching an end seal to a manufactured seed, the method comprising the steps of:
   (a) positioning a manufactured seed on a surface, the manufactured seed including a seed coat having an opening and an embryo disposed within the opening, the opening having a location relative to the surface;
   (b) ablating a predetermined area of a sheet;
   (c) positioning the sheet on the manufactured seed to substantially center the predetermined area over the opening such that the embryo is located below the predetermined area;
   (d) attaching the sheet to the first manufactured seed to seal the opening;
   (e) forming a dimple in the predetermined area of the sheet before ablating the predetermined area; and
   (f) placing the sheet between first and second templates before ablating the predetermined area of the sheet, the first and second templates each having a bore extending therethrough.

25. The method of claim 24, wherein the predetermined area of the sheet is located according to the location of the opening of the seed coat.

26. The method of claim 25, wherein the step of ablating the predetermined area of the sheet forms an annular collar on at least one surface of the sheet.

27. The method of claim 26, wherein the step of attaching the sheet to the manufactured seed includes fusing the sheet to the manufactured seed to seal the embryo within the manufactured seed.

28. A manufactured seed, comprising:
   (a) a seed coat having a length and a cavity extending from one end of the seed coat partially through the length of the seed coat, the cavity having an open end and a closed end;
   (b) an embryo disposed within the cavity; and
   (c) an end seal attached to the one end of the seed coat, the end seal having at least one a prestressed area, the prestressed area being located on a predetermined portion of the end seal to position the prestressed area substantially over the opening of the cavity, wherein the prestressed area includes an annular collar formed in at least one surface of the sheet, wherein the annular collar is at least partially received within the cavity to form a seal between the end seal and the cavity.

29. The manufactured seed of claim 28, wherein the prestressed area is centrally located in an indentation formed in the predetermined portion of the end seal.

* * * * *